United States Patent [19]

Sump

[11] Patent Number: 4,644,942
[45] Date of Patent: Feb. 24, 1987

[54] PRODUCTION OF POROUS COATING ON A PROSTHESIS

[75] Inventor: Kenneth R. Sump, Richland, Wash.

[73] Assignee: Battelle Development Corporation, Richland, Wash.

[21] Appl. No.: 569,199

[22] Filed: Jan. 9, 1984

Related U.S. Application Data

[63] Continuation-in-part of Ser. No. 401,112, Jul. 23, 1982, which is a continuation-in-part of Ser. No. 287,166, Jul. 27, 1981.

[51] Int. Cl.⁴ .................................................. A61F 5/04
[52] U.S. Cl. ............................................ 623/16; 419/2; 419/8; 419/36; 419/37; 419/49; 427/2; 427/180; 427/191; 427/201; 428/550; 428/926
[58] Field of Search ............... 128/92 C, 92 G; 427/2, 427/180, 191, 201; 419/8, 2, 36, 49, 37; 428/550, 926

[56] References Cited

U.S. PATENT DOCUMENTS

| | | | |
|---|---|---|---|
| 3,905,777 | 9/1975 | Lacroix | 428/550 |
| 4,017,911 | 4/1977 | Kafesjian et al. | 428/548 |
| 4,073,999 | 2/1978 | Bryan et al. | 428/548 |
| 4,156,943 | 6/1979 | Collier | 419/55 |
| 4,309,488 | 1/1982 | Heide et al. | 428/547 |
| 4,374,669 | 2/1983 | MacGregor | 419/9 |

Primary Examiner—Stephen J. Lechert, Jr.
Attorney, Agent, or Firm—Wells, St. John & Roberts

[57] ABSTRACT

Preselected surface areas of a prosthesis are covered by a blend of matching primary metallic particles and expendable particles. The particles are compressed and heated to assure that deformation and metallurgical bonding occurs between them and between the primary particles and the surface boundaries of the prosthesis. Porosity is achieved by removal of the expendable material. The result is a coating including discrete bonded particles separated by a network of interconnected voids presenting a homogeneous porous coating about the substrate. It has strength suitable for bone implant usage without intermediate adhesives, and adequate porosity to promote subsequent bone ingrowth.

25 Claims, 20 Drawing Figures

U.S. Patent  Feb. 24, 1987  Sheet 1 of 10  4,644,942
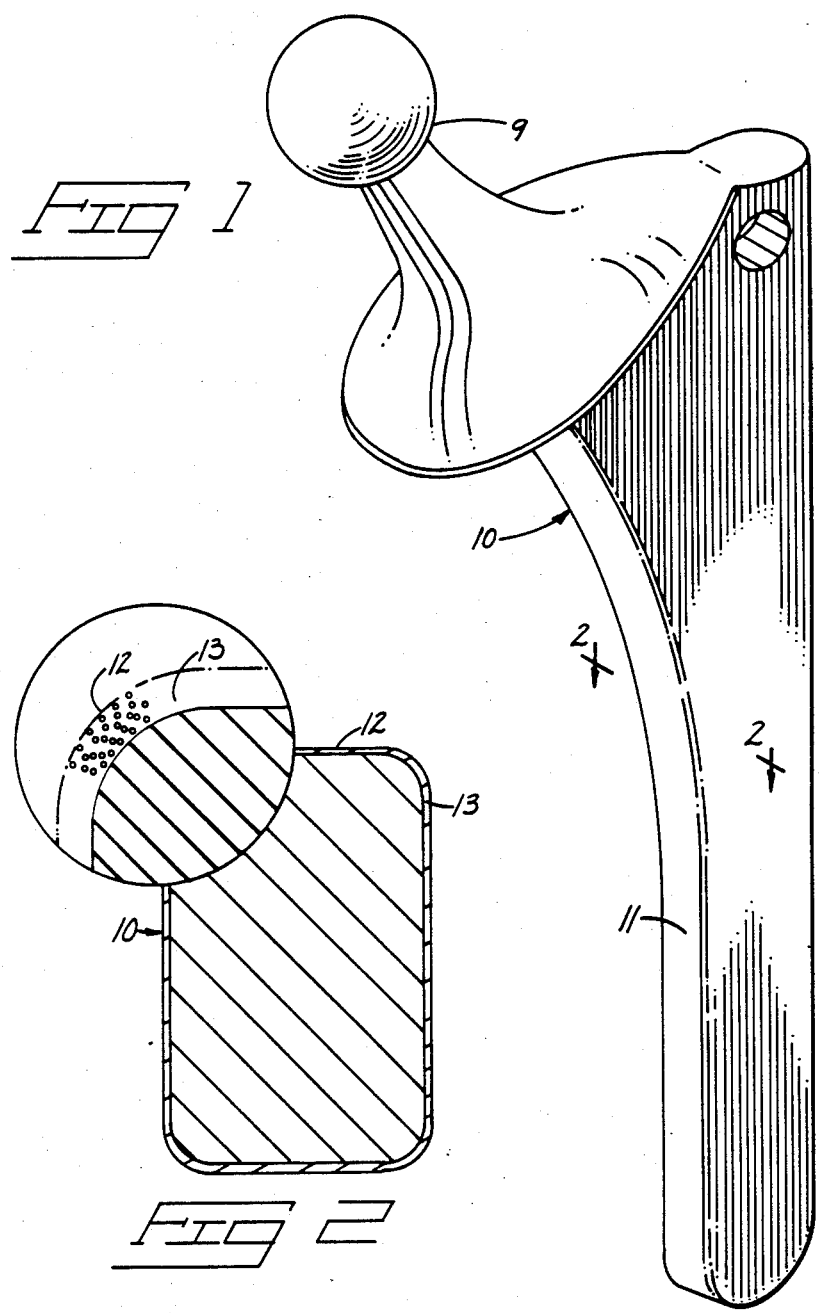

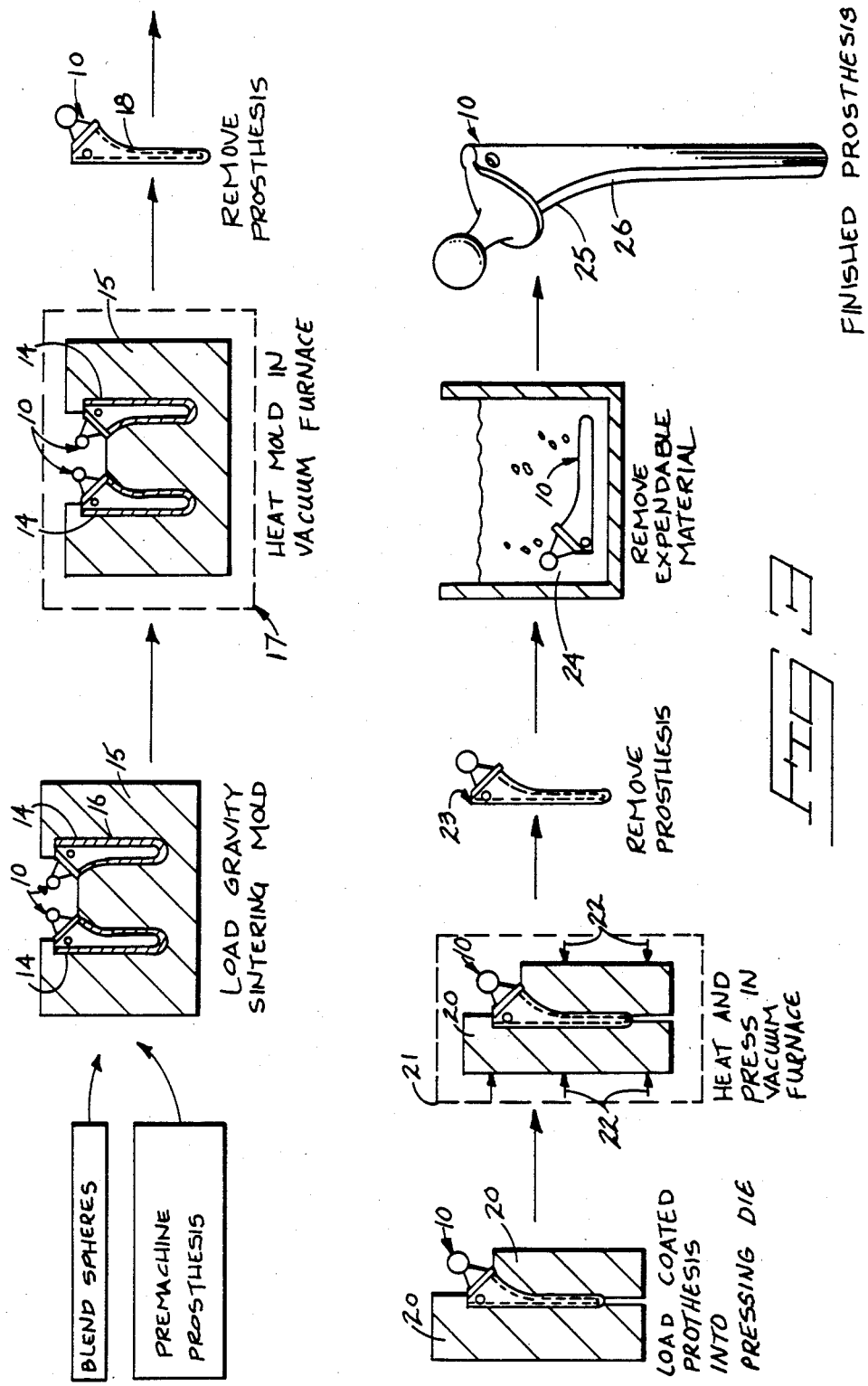

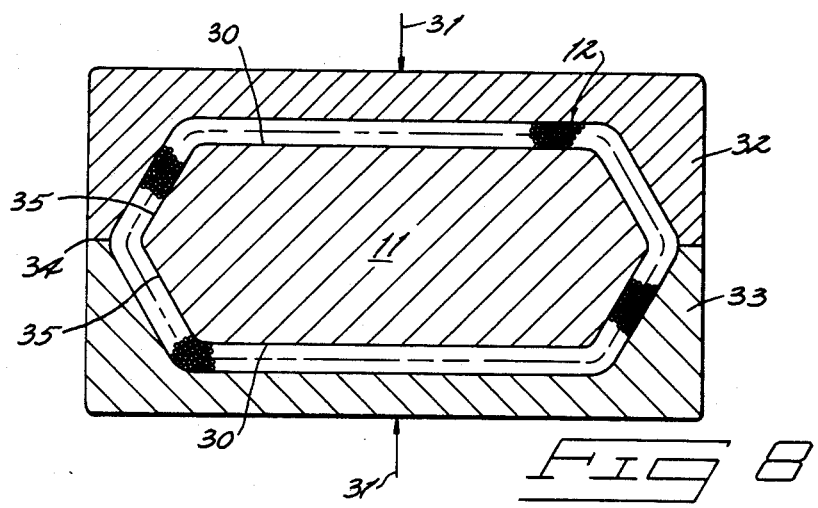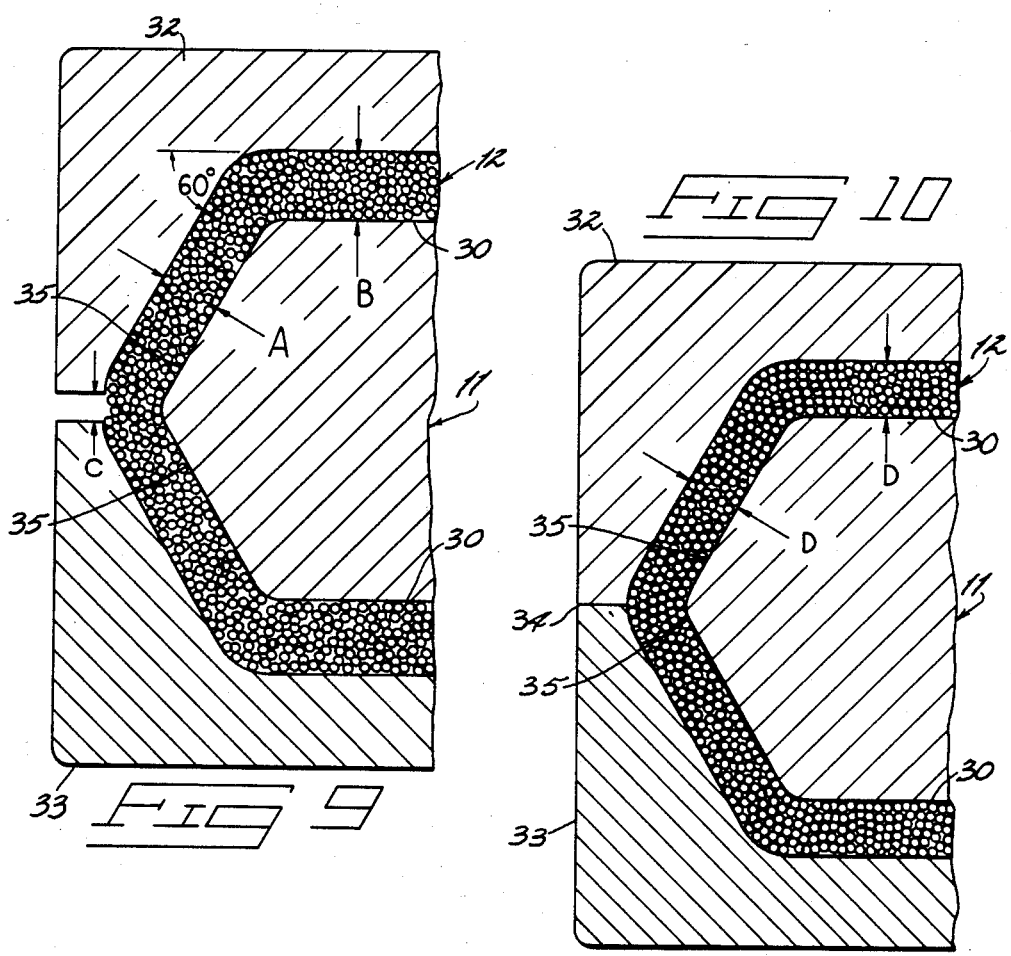

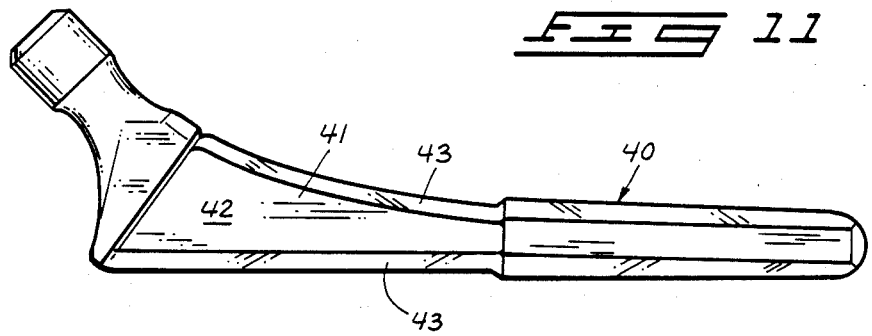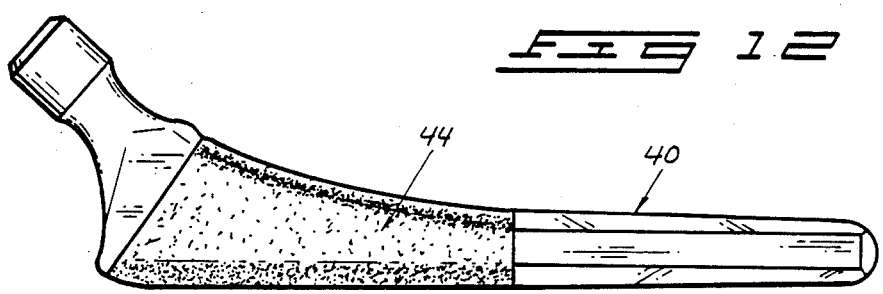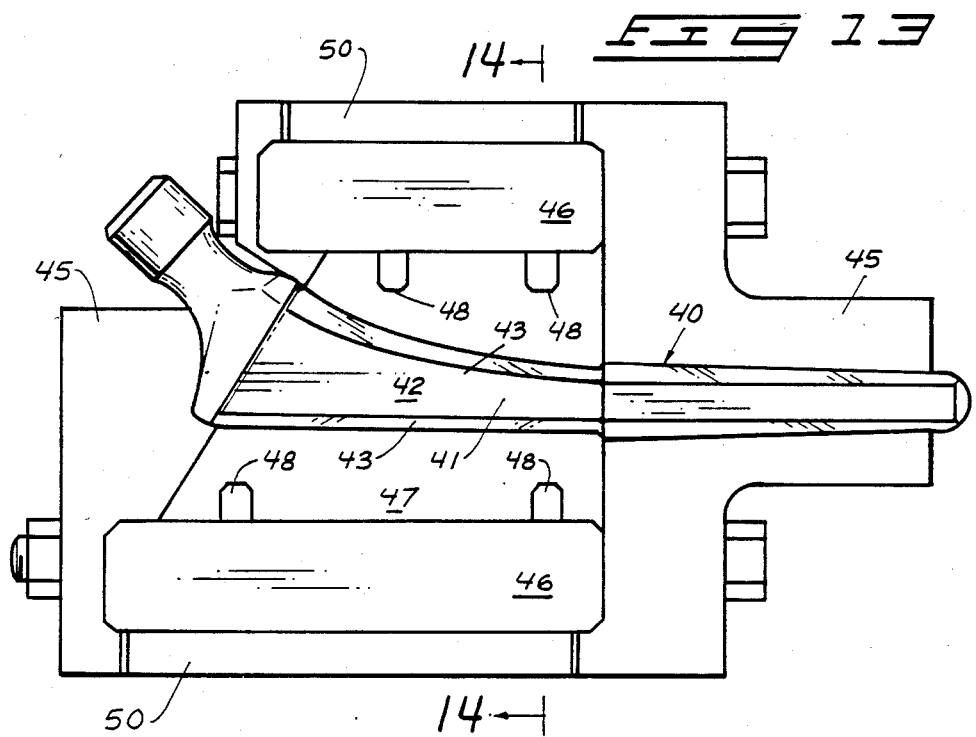

FIG 17

BLEND Ti6Al4V AND Fe
MICROSPHERES WITH BINDER

↓

LOAD IN HOT PRESS TOOLING
AROUND SUBSTRATE

↓

VACUUM HOT PRESS
850°C, 10,000 POUNDS

↓

REMOVE PROSTHESIS
AND SHAPE TO FINAL FORM

↓

ETCH TO REMOVE
Fe MICROSPHERES

↓

PROSTHESIS WITH
~50% DENSE, 1 mm THICK,
Ti6Al4V COATING

FIG 19

LOAD TOOLING IN HOT PRESS

↓

EVACUATE CHAMBER

↓

HEAT TO 850°C UNDER
NO LOAD CONDITIONS

↓

APPLY 10,000 POUND LOAD
FOR 30 MINUTES AT
TEMPERATURE

↓

REMOVE LOAD

↓

COOL FURNACE

↓

REMOVE DIE FROM HOT PRESS

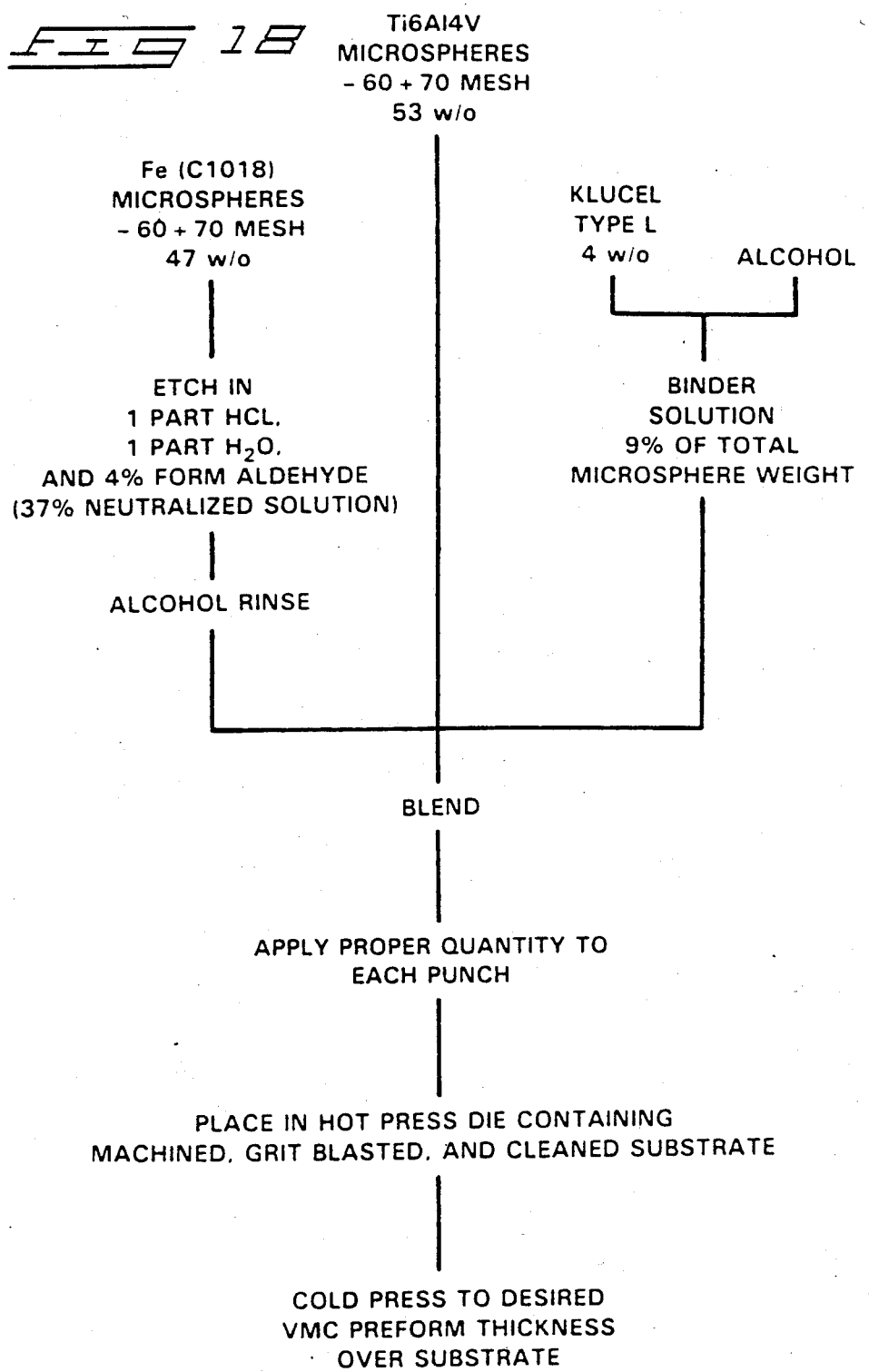

PRODUCTION OF POROUS COATING ON A PROSTHESIS

RELATED PATENT APPLICATIONS

This is a continuation-in-part of co-pending U.S. patent application, Ser. No. 401,112, filed July 23, 1982, which in turn was a continuation-in-part of application Ser. No. 287,166, filed July 27, 1981.

TECHNICAL FIELD

This disclosure relates to the coating of preselected metallic surface areas on a prosthesis for subsequent tissue ingrowth applications. The coating is in the form of a porous material having interconnected pores through which hard or soft body tissues can grow.

BACKGROUND ART

U.S. Pat. No. 3,855,638 to Pilliar discloses a surgical prosthetic device that consists of a solid metallic material substrate with a porous coating over at least a part of its surface. The coating has a thickness between one hundred to one thousand microns. The coating is formed from metallic powder sized between −100 to +325 mesh. The patent discloses production of the coating by using a slurry of metallic powder suspended in an aqueous solution with organic binders. The particle size of the metallic powder and conditions of formation of the porous coating are controlled to provide the desired interstitial pore size, porosity, strength and depth of coating. Both the substrate and powder are sintered to achieve metallurgical bonding between engaged metal particles and between the metal particles and the substrate. The disclosure states it to be essential that the porosity of the surface coating not exceed about 40% and be at least about 10%. It states that a porosities above 40% the overall mechanical strength falls below the required level.

U.S. Pat. No. 3,852,045 to Wheeler, Sump and Karagianes, discloses a porous metallic material with interconnected voids, again directed to tissue ingrowth purposes. Voids or pores are produced in the metallic material by use of expendable void formers. The composite material is treated by high energy rate forming pressures to densify its structure prior to removal of the expendable void former. Substantial thicknesses of the coating on substrate metallic elements are disclosed.

While the products resulting from the systems taught in U.S. Pat. No. 3,852,045 have performed satisfactorily, the practical application of the system is severely limited by both the expense and availability of equipment for the required high energy rate forming steps. Furthermore, such steps are of questionable value when attempting to produce a relatively thin porous coating on implant elements, since the high pressures to which the elements would be subjected might result in structural damage to them.

According to the present invention, relatively thin porous metallic coatings are produced about selected surface area configurations on a prosthesis by forming the coating about the surface, using a blended mixture of primary and secondary particles. The primary particles are either made from a material identical to or metallurgically compatible with the metallic surface being coated. The secondary particles are made of an expendable material. Both are heated and pressed in place about the surface to effect metallurgical bonding between engaged primary particles as well as between the surface area and the primary particles in contact with it. The expendable material is subsequently removed to achieve controlled porosity throughout the coating.

DISCLOSURE OF INVENTION

The basic method of this invention comprises the steps of covering a preselected metallic surface area of a prosthesis with a blended mixture of primary and secondary particles, reducing the dimensional thickness of the mixture by compressing it against the surface, simultaneously applying heat to form metallurgical bonds between primary particles, and subsequently removing the expendable secondary particles to present a homogeneously porous coating on the metallic surface area.

The method of covering the metallic surface area can be accomplished by first loading a mold by positioning the prosthesis with the preselected surface area or substrate spaced inward from the mold cavity surfaces. The space between the substrate and the mold cavity surfaces is then filled by injection or spreading of a blended mixture of primary particles identical to or metallurgically compatible with the metallic surface area of the bone implant element and secondary particles of expendable material in a packed volume containing random shaped voids between the particles. These steps can be carried out in a gravity mold or can be accomplished in the pressure molding apparatus where subsequent compression of the coating occurs. The blend of particles can be applied within a gravity or compression mold in a dry condition or can first be mixed with a liquid binder to assist in maintaining it in a homogeneous condition. The blend of particles containing a binder can also be applied by other suitable coating processes.

Due to the dimensional limitations presented when producing relatively thin porous coatings about the surfaces of a prosthesis, injecting a blended mixture of particles between the substrate surfaces and mold cavity is often impractical. In such instances, the particles and a liquid binder can be adhered to the substrate as the mold is being assembled. As an example, a mixture of particles and binder might be spread over the mating surfaces of movable pressure jaws while the jaws are being positioned in a die assembly.

If a time delay is to occur between the covering of the substrate and the final bonding of the particles, the blend of particles can be initially adhered to one another and to the surface by light sinter bonds between primary particles when no binder is present or by curing or drying of the binder, when a binder is included with the particles.

The particles are next heated to an elevated temperature at which metallurgical bonding will occur between them due to a combination of heat, pressure, and mechanical deformation. The coating is compressed against the prosthesis while at the elevated temperature to reduce the dimensional thickness of the coating and to reduce the controlled volume percentage of random shaped voids that will ultimately remain in the coating.

As a final step, the expendable material is removed from the coating. The resulting porous coating will have a surface configuration complementary to the mold. Controlled porosity throughout the coating results from a combination of the interstitial spaces between the initially-bonded primary and secondary particles after heating and while under pressure, as well as the voids that remain within the network of bonded primary particles after removal of the expendable secondary particles.

The prosthesis produced according to this disclosure includes a metallic substrate and a coating of randomly dispersed metal particles. The particles are of substantially uniform size and are joined to one another and to the substrate by metallurgical bonds. The outermost particles are compressibly deformed and dimensioned for implant usage. The metal coating particles are separated by a network of interconnected voids having an average size greater than the average size of the metal particles to present a homogenously porous coating about the substrate.

It is an object of this method to achieve controlled pore size and morphology in a porous coating comprising discrete particles joined by metallurgical bonds.

Another object is to provide porosity in the coating in excess of 40%, while achieving successful metallurgical bonding between the particles themselves as well as between the particles and the substrate, by a combination of mechanical compression and application of heat under controlled conditions such that a prosthesis will be covered by a coating having adequate strength for practical use in implant applications.

Another object is to combine pressures of a magnitude to effect mechanical deformation and thermal bonding of particles so as to successfully coat implant surfaces with minimum temperature elevation, thereby preserving the metallurgical structure and properties of the substrate through the coating procedure.

Another object of this invention is to provide a practical thin porous coating on metallic surfaces of a prosthesis in a manner which retains the complex surface configurations often required about the surfaces.

Another object is to provide an effective method of controlling final coating density and porosity so as to permit accurate design of the coating structure for tissue ingrowth requirements.

Another object is to produce a coated implant surface by compressive molding techniques in a manner that assures attainment of rigid exterior tolerances without requiring machining of the coated surfaces.

Finally, an object of the invention is to develop a practical process and product by use of available techniques, equipment and raw materials.

DESCRIPTION OF THE DRAWINGS

FIG. 1 is a perspective view of an implant element having porous coated surfaces;

FIG. 2 is an enlarged fragmentary transverse sectional view taken substantially along line 2—2 in FIG. 1, with a circled corner area further enlarged for illustration;

FIG. 3 is an illustrative flow diagram showing the steps of the present process;

FIG. 8 is a schematic cross-sectional view illustrating molding of the coating;

FIG. 9 is a partial schematic cross-sectional view of the open compression mold;

FIG. 10 is a similar view of the closed mold;

FIG. 11 is a side view of a second form of a hip prosthesis prior to coating;

FIG. 12 is a side view after coating;

FIG. 13 is a plan view of a partially assembled die;

FIGS. 17–20 are flow diagrams detailing the steps of the process.

BEST MODE FOR CARRYING OUT THE INVENTION

Figure 4:
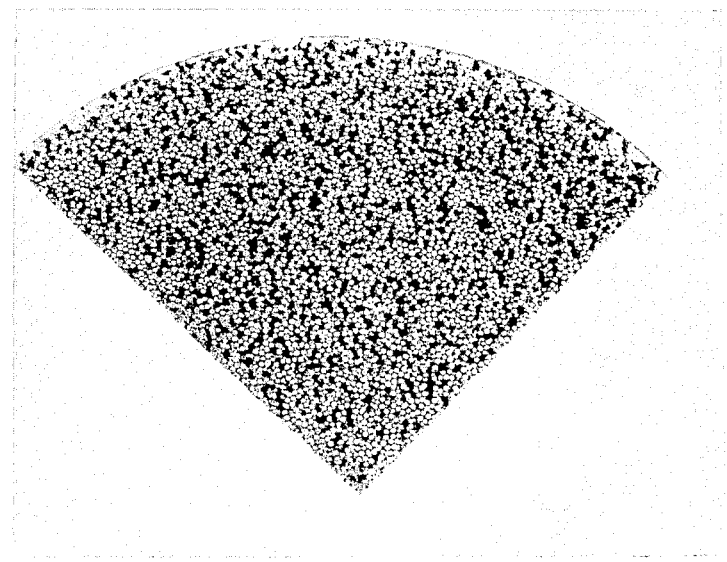
FIG. 4 is a plan photograph showing the outer coating surface after removal of the expendable material.

FIGS. 1 and 2 generally illustrate a known configuration of a hip prosthesis 10. The prosthesis 10, which is a relatively common bone implant used in surgical repair of hip joints, includes an elongated shank 11 intended to be inserted axially within a supporting bone structure. It is capped by a ball structure generally shown at 9. In most surgical installations of such a prosthesis, the shank 11 is anchored to the bone structure by bone cements.

As illustrated in FIGS. 1 and 2, the outer surfaces of the shank 11 are covered by a porous metallic coating 12 that surrounds an inner solid metal substrate 13. The coating 12 is bonded to the substrate 13, and includes interconnected pores through which soft and hard living tissues can grow after implantation of the prosthesis 10.

The present process is initiated by cleaning and machining of the preselected metallic surface areas upon which the coating is to be formed. Additionally, the particles to be used in the coating must be intimately blended to produce a relatively homogenous mixture of the primary particles of metallic material matching or metallurgically compatible with the surface area and the secondary particles of expendable material. It is preferable, but not required, that the particles of both materials be of identical size. This will result in substantially constant porosity throughout the final coating. It also assures that the maximum number of contacts will occur between each particle and those surrounding it. The particles within both the primary and secondary materials should be restricted to a relatively narrow size range within the limits of 35 mesh (500 microns) and 80 mesh (177 microns); e.g., −60 +70 mesh (210 to 250 microns). These particle sizes have practical application in the development of porous coatings having a thickness of between 500 to 1,000 microns, which would then have a thickness of from three sphere diameters to about six sphere diameters. Obviously, coatings of greater thickness can be produced when desired.

When utilizing a dry blend of particles, the surfaces of prosthesis 10 which are to be coated are next positioned within a precision mold cavity 14 in a gravity sintering mold 15. The preselected metallic surface areas to which the coating is to be affixed must be spaced inwardly from the mold cavity surfaces 14. The spacing between the surfaces will be dependent upon the desired thickness of the final coating, and the amount of coating compression which will be accomplished in subsequent steps described below.

As indicated by arrow 16 in FIG. 3, the blended mixture of primary and secondary particles must be fed or injected into the spaces between the stationary mold cavity and the prosthesis. The mold 15 is next subjected to heat within a furnace indicated generally at 17. Furnace 17 is preferably a vacuum furnace, since vacuum pressure during the heating step inhibits oxidation of the metallic alloys. Oxidation can also be minimized or prevented by heating the mold within a suitable inert atmosphere. The temperature of the particles surrounding the prosthesis should be raised to a level at which minimal metallurgical bonding between adjacent particles will be achieved, as well as bonding of the particles to the substrate area. The temperature should be maintained below that at which any adverse reactions will occur with the expendable phase. In the case of prosthetic surfaces and spherical particles made from Ti-6A14V alloy (6% Aluminum, 14% Vanadium, the balance being Titanium) with copper or iron as the expendable phase, the bonding temperature will be maintained below the beta transus temperature for the alloy (for example, 970° C.).

As indicated at numeral 18 in FIG. 3, the prosthesis 10 can then be removed from the gravity sintering mold as a "preform" with a coating of the gravity sintered particles formed about it. Were the expendable phase material to be removed at this stage of product manufacture, the resulting porous coating provided by the remaining spheres would have inadequate strength for surgical implant purposes.

As an alternative to this initial sintering step, the preform can also be produced by use of a binder mixed with the original blend of particles. Details of such binder usage are set out below.

To assure adequate strength properties in the final coating, deformation pressures are applied between the heated metallic spheres by pressure molding. This can be achieved by use of any pressure molding apparatus capable of accurately deforming the complex surface areas under controlled conditions to achieve reproducible coatings on the manufactured bone implant elements. While a hot isostatic pressing apparatus might be used, the specific illustration shown in FIG. 3 shows use of mechanical dies having two or more jaw segments for compression of the coating surface areas.

The preform 18 or coated prosthesis is placed within the complementary jaws 20 of a pressing die, with the die cavity surfaces overlying the preselected surface areas of the prosthesis to be coated. The die jaws 20 and prosthesis are then subjected to heat within a furnace 21. Furnace 21 again is either a vacuum furnace or a furnace having a supply of inert gas to minimize or prevent oxidation of the metallic alloys. The temperature of the spherical particles surrounding the prosthesis must again be raised to one at which some metallurgical bonding between adjacent primary particles and between the primary particles and underlying substrate will occur. The prosthesis is then subjected to surface compression by movement of the jaws 20 as indicated as arrows 22. This compression step should typically reduce the volume of the coating about the prosthesis surfaces by 10% to 30%. This in turn reduces the dimensional thickness of the mixture of particles to the desired final coating thickness.

The process is completed by removing the prosthesis from the pressing die. The prosthesis will have the pressed coating of desired metal and expendable material formed about it. This condition of the prosthesis is shown at 23 in FIG. 3. Substantial metallurgical bonds will now exist between the primary coating particles, with some surface deformation both between the spheres of the desired matrix metal and also between the prosthesis substrate and those particles in engagement with it.

The production of the porous coating is completed by chemically removing the expendable phase in a liquid bath shown at 24. The result is the prosthesis shown in FIG. 3 at 25, which now has an accurately controlled porous coating 26 securely formed about the preselected surface areas. Such a coating will permit bone ingrowth after surgical implantation.

The materials used in this process must be selected so as to be compatible with the materials of the prosthesis (capable of metallurgical bonding without adverse effect) and the processing requirements during coating formation. The primary coating material will normally be selected to match the metallic material of the preselected surfaces to be coated on the prosthesis. However, other materials having suitable bonding compatibility, and which are biologically acceptable, might be used in certain instances.

It is anticipated that the expendable particles will normally be metallic. Examples of materials usable for this purpose are particles of copper, iron, steel, or molybdenum. Metals and alloys must be used which can be readily removed after the production of the coating has been completed. Low temperature eutectic reactions with the prosthesis and primary metallic particles should be avoided.

The mechanical deformation pressure that occurs between the primary metal particles hastens development of metallurgical bonds at temperatures substantially lower than those that would be required in the absence of compression. While compressive deformation of the primary metal particles is of primary importance with respect to the strength properties of the final coating, it is to be understood that mechanical deformation can also occur in the expendable particles and at the surface of the substrate.

It is preferable that the coating be produced on the substrate by application of pressure only while the substrate and coating materials are at the selected elevated deformation pressure.

The main reason for not applying pressure during the preheating is that this would increase the amount of coating material lost at the parting line of the two die jaws. The microspheres might not be well bonded during preheating and any binder used will be vaporized. Constant pressure below temperature could cause microsphere flow.

The main reason for not leaving the pressure applied during cooling is that in the pressing at temperature the punches and die are "bottomed out" to a known height. When cooled, the surrounding die might become shorter than the movable jaws due to differential thermal expansion. At temperature, only as much of the overall pressure as necessary is used for densification and the remainder is absorbed by the die. Once cooling begins, the entire load might be supported by the movable jaws as the temperature is reduced. Over-densification, as well as loss of dimensional tolerances, could occur.

A significant advantage of this process is the ability to produce an effective porous coating at relatively low temperatures in comparison to usual gravity sintering. This is achieved within reasonably short time spans by combining both mechanical pressure and thermal deformation of particles and substrate to achieve metallurgical bonds. The use of low sintering temperatures is of particular importance when bonding a coating to a substrate which would be modified metallurgically by elevation to higher temperatures.

As an example of a practical blend of particles for coating surfaces made from a titanium alloy (Ti6A14V), the blend of materials in the gravity sintering step might comprise 45% by volume Ti6A14V spherical particles and 20% by volume expendable spherical particles. The remaining space between the prosthesis surfaces and the surrounding mold cavity will be void space between the spheres. These voids will equal 35% of the coating volume. After the coating has been compacted, heated and pressed, the volume percentage of Ti6A14V spheres will be 50%, the volume percentage of expendable spheres will be 22.2%, and the void volume will be reduced to 27.8%. Removal of the expendable material from the resulting coating will produce a final porous coating of approximately 50% density, meaning that the interconnecting pores formed throughout the coating occupy 50% of the total coating volume.

Varying the size and/or percentage of the primary spherical particles with respect to the expendable spherical particles can be utilized as a production control to select the structure and density of the resulting coating on the prosthesis.

Spherical particles are preferred as starting materials for production of the coating, but spherical particle shapes are not essential to practice of the invention. Spherical powders of the required metallic materials are readily available in closely defined size ranges. They are also easily handled and packed with minimum damage and resulting dust. By using spheres of the same diameter for both the primary and expendable materials, one can maximize the theoretical number of contact locations to be expected between adjacent particles. This leads to greater bonding of the primary particles and improved strength in the final coating. However, non-spherical granular or particulate powders of either the primary or expendable material can be utilized when available.

Voids in the final coating are attributable to both the spaces initially occupied by the particles of expendable material (spherical voids) and the spaces between the adjacent particles of both materials (random shaped voids). The number and size of the spherical voids is determined by the number and size of the expendable particles, which are essentially unchanged during compression of the coating. The volume percentage of the random shaped voids is decreased during compression, primarily due to deformation of the primary material particles against one another, against the expendable material particles, against the substrate surface, and against the outer die surfaces.

The method of this invention reduces the void volume in the covering blend of particles, but does not eliminate it. The void volume can be either totally empty or can be partially or completely filled by a binder or other liquid. The maintenance of a void volume assures that the primary particles can remain as discrete particles after deformation and that deformation of the secondary particles will not flow into areas of contact between adjacent primary particles so as to disturb the desired metallurgical bonds being formed between them.

The spherical voids, which are ultimately integrated with random shaped voids as well, are important for tissue ingrowth. They guarantee that the resulting coating will contain interconnected larger irregular voids between the discrete primary particles. The final voids will have an average size greater than the average size of the particles, assuming the primary and secondary particles to have initially been essentially identical in size. The interconnection between such voids presents effective pathways for tissue growth.

The random shaped voids guarantee a continuous network of voids in the coating prior to removal of the expendable material. This permits removal of the expendable material through the void network, whether by etching, application of heat, or by any other suitable method. In general at least a 5% void volume will be required in the compressed coating to assure complete removal of the expendable material.

Another important feature of the coating is the fact that its outer surfaces are mechanically deformed against the outer die surfaces within which it is compressed. By utilizing compression dies pressed against fixed stops which define the limits of compression, one can accurately manufacture a coated element having the outer dimensional tolerances required in bone prosthesis applications and similar usages. The compressed outer coating surfaces are free of burrs, rough edges and particle remnants which might be presented after surface machining operations.

In general, a coating having approximately 50% density (50% solid volume, 50% void volume) is desirable for tissue ingrowth applications. The percentage of densification can vary between different surfaces on an element, depending upon their relative orientations and complementary die opening design. For illustration, FIGS. 8-10 schematically show compression molding at a cross-section of shank 11 defined by normal surfaces 30 which are perpendicular to the directions in which pressure is applied (arrows 31) by a split die 32,33. Surfaces 30 are joined by angular surfaces 35 along the edges of shank 11 which are arranged at an angle of 60° relative to the normal. The following illustration shows the effect of compression. It assumes the use of a split die 32, 33 having a seam 34 midway between and parallel to the normal surfaces, dimensioned to produce a compressed constant depth of coating on all surfaces when fully closed.

The original coating thickness B about the normal surfaces 30 is 0.0533 inches (1.35 mm). When compressed, the final coating thickness D is 0.040 inches (1.02 mm). The corresponding original coating thickness A about the angular surfaces 35 should be 0.0467 inches (1.186 mm) to achieve the same final coating thickness D in this die configuration. The die spacing C is 0.0267 inches (0.68 mm). The coating material on the normal surfaces 30 will be compressed by 25% and the coating material on the angular surfaces 35 will be compressed by 14.3%.

The original blend of spherical particles coating all surfaces is 40% primary metal (Ti6A14V), 20% expendable metal (Iron) and 40% voids, by volume. After compression to stops defining the final 0.040 inch coating thickness, the coating at the normal surfaces will comprise 40% primary metal, 20% iron and 15% voids, by volume. The coating at the angular surfaces will also be 40% primary metal and 20% iron, but the voids will be 21.7%, again by volume. After removal of the expendable metal, the volume of primary metal content of the coating on the normal and angular surfaces will then comprise 53.5% and 46.7% of total coating volume, respectively.

In tabular form, such densification can be illustrated as follows:

|  | Packed Blend (% vol) | → | Hot Press | → | Acid Etch |  |  |
|---|---|---|---|---|---|---|---|
| Normal Surfaces | 40 Ti6A14V | →40 |  | →40 |  | = | 53.3% |
| (25% Densification | 20 Fe | →20 |  | →20 | Void |  | solids |
| 0.0533 in 0.040 in) | 40 Void | →15 | Void | →15 | Void |  | by vol. |
| Angular Surfaces (60°) | 40 Ti6A14V | →40 |  | →40 |  | = | 46.7% |
| (14.3% Densification | 20 Fe | →20 |  | →20 | Void |  | solids |
| 0.0467 in 0.040 in) | 40 Void | →25.7 | Void | →25.7 | Void |  | by vol. |

In the initial filling of the mold or die cavity, the particles must be closely packed so as to substantially fill its volume without mechanical deformation occurring. This assures the greatest number of particle contacts by each particle in the blend, both primary and expendable. After compression, the volume of coating is substantially reduced by partial elimination of the void between adjacent particles as a direct result of the deformation of the primary particles. By compressing the coating to fixed stops, excess pressure can be used, and accurate coating thickness and surface control is assured.

It should be noted that initial gravity sintering, when utilized, can be accomplished in the compression die used to ultimately press the coating about the preselected metallic surfaces. While it is convenient to produce a preform in a mold having no seams, the separate production of the preform is not essential to the disclosed process.

As an alternative to initial gravity sintering, either in a separate mold or in the compression die, this step can be totally eliminated by use of a binder in the original blend of particles. An important benefit achieved by using a binder is the fact that the two different types of particles can be uniformly blended with the binder and will not subsequently tend to segregate as they are being placed in the mold or die cavity. Such segregation must be avoided when the particles are dry, making storage and handling of the blended particles more difficult.

Binders are preferably water-based and capable of being heated to approximately 350°–500° F. (180°–270° C.) to remove water content and leave a residue layer that bonds the particles together. This remaining material in turn must volatilize at a temperature below the selected sintering temperature for the coating.

Binder materials tested to date include cellulose gum powders, polyvinyl pyrrolidone, hydroxypropyl cellulose, polyethylene glycol, and polyvinyl alcohol. These were used at concentrations between 0.5 g to 8.0 g in 200 cc of water. Other organic binders can be selected for use in blending and handling the particles, and they can be mixed with solvents other than water, so long as the binder is inert relative to the particles.

The amount of binder added to the blend of particles must merely be sufficient to coat their surfaces and prevent their segregation during handling and placement on the substrate. No particular volume relationships are required.

The use of a binder permits one to produce a green, uncompacted coating without compression or sintering. After curing or drying the binder, the particles will be adhered to the prosthesis surfaces and the coated element can be stored or handled as required by production techniques. The binder also facilitates introduction of the homogeneously blended particles directly into the compression dies, assuring uniform distribution of primary and expendable particles about closely restricted areas separating substrate surface and outer die surfaces.

It is also preferable that the mold cavities and dies be produced with sufficient precision as to obviate the need for any finish machining of the coating surfaces. However, should machining steps be required, they would normally be accomplished prior to removal of the expendable phase.

As an example of the removal of the expendable phase, the expendable material discussed in the above example can be chemically removed by immersion in a bath of suitable acid. The finished product would subsequently be treated to a low temperature vacuum outgassing to assure removal of any non-metallic contaminants.

EXAMPLE 1

In a specific test of the process which led to this disclosure, a disk of titanium alloy (Ti6A14V) was coated with a porous cover of microspheres of the same alloy. The coating was approximately 1.25 millimeters thick. The primary microspheres were between −40 and +80 mesh (177–420 microns). The expendable copper microspheres were of an identical size range. A sintered preform was not used. The composite coating was fabricated by hot pressing at 850° and 2,000 psi in an argon atmosphere. The copper microspheres were removed in dilute nitric acid. The density of the coating was 48% by volume of the theoretical volume of the coating total. Resulting metallography of the sample showed clear evidence of bonding between the titanium alloy microspheres and to the titanium alloy disk.

EXAMPLE 2

In another experiment designed to demonstrate that gravity sintering of microspheres would form a suitable preform for subsequent hot pressing, titanium alloy (Ti6A14V) microspheres were gravity sintered about a titanium alloy (Ti6A14V) rod in an aluminum oxide crucible. Sintering was accomplished in vacuum at 1,025° C. for one hour. The resulting part evidenced sufficient strength in the coating to serve as a preform. No further processing of this sample was accomplished.

EXAMPLE 3

Test have been conducted to demonstrate coating of substrate material typically used in hip implants as generally shown in FIGS. 1 and 2. This comprised a 0.078 in (1.98 mm) thick, circular disk of Ti6A14V alloy. It had an alpha structure content.

The titanium alloy (Ti6A14V) spheres used as primary particles for the coating were −60 +70 mesh spheres. They had an alpha structure content. Iron spheres of the same size range were of C1018 iron, containing 0.20% oxygen by weight and 0.84% manganese, the balance being iron.

A cellulose gum binder in water (3 g/200 ml) and a similar concentration of polyvinyl alcohol were separately blended with titanium and iron spherical particles and placed at opposite sides of the titanium disk in a hot press die. They were first hot pressed at 900° C. at a pressure of 1000 psi for about 1 hour, but this pressure was inadequate to achieve full closure of the die. The assembly was subsequently hot pressed at 900° C. at a pressure of 2000 psi for approximately another hour. Complete movement of the dies to a predetermined stop position was accomplished, resulting in the desired densification of the coating.

The disk of titanium alloy had at least two good layers of spherical particles bonded to it. The disk was cut and two quadrants were placed in dilute nitric acid to remove the iron spheres. The total coated sandwich was 0.167 in (4.24 mm) thick. Evaluation was conducted primarily by metallography. FIG. 4 shows a top view of one coated surface after removal of the expendable iron spheres. Good distribution of the light-colored remaining discrete particles is evident.

Figure 5:
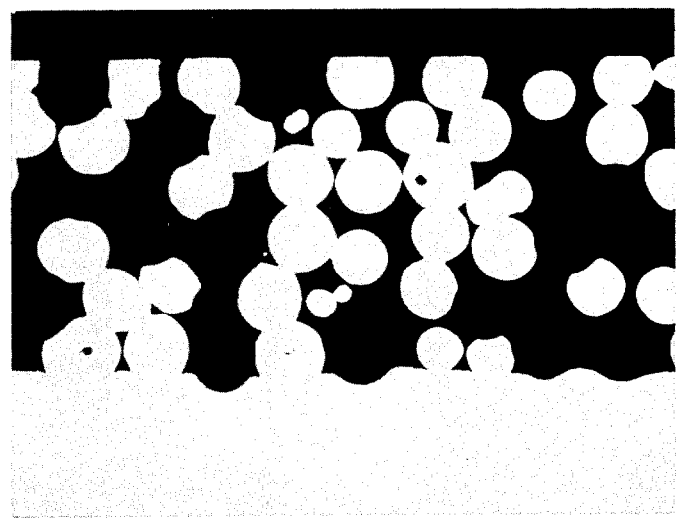
FIG. 5 is an enlarged (50×) side view of a cross-sectional slice through the coating and substrate in FIG. 4.

FIG. 5 shows an enlarged side view along one cut surface or edge of the substrate. Some of the bonded spherical particles (light-colored circles) shown in FIG. 5 have a smaller diameter because they were not sliced through their centers. The deformation and relatively wide compressed bonds formed between contacting discrete spherical particles is evident as they form a lattice of connected spheres. The deformation of the boundary layer of spheres against the substrate shown across the lower portion of FIG. 5 in this instance was substantial. Substrate deformation was also evident from the indentations or dimples which remain after removal of the iron spheres. The even compression of the outermost layer of spheres across the top of FIG. 5 shows the compressive effect of the die surface in forming an outer surface of uniform depth and accurate tolerance along a prescribed plane.

FIG. 5 graphically illustrates the desirable interconnected voids (dark areas) between the bonded particles. These can be seen to be an accumulation of the random void spaces or void volume which remain between adjacent titanium spheres, and the larger spaces which include the original positions of the iron spheres plus the random voids which were located about them. It can be readily seen that the result is that the metal particles in the coating are separated from one another by a network of interconnected voids having an average size greater than the average size of the discrete metal particles or spheres in the original blend of spheres introduced into the die.

Figure 6:
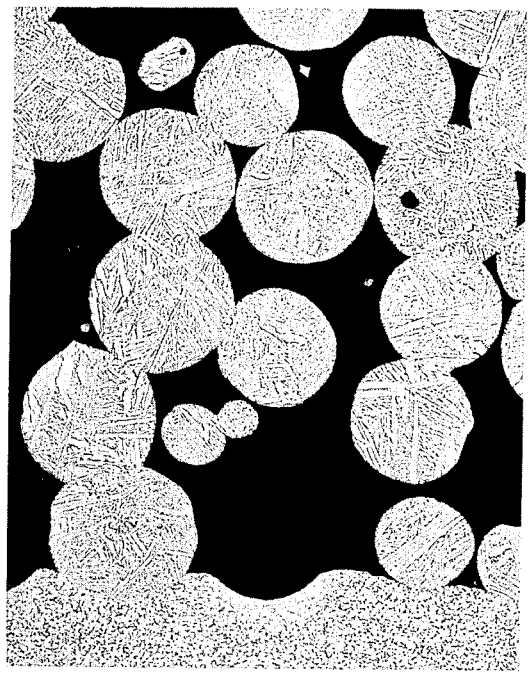
FIG. 6 is an enlarged (100×) side view taken at the center of FIG. 5 after etching out the grain structure of the coating and substrate.

FIG. 6 is a further enlargement of the central portion of FIG. 5 after etching of the surface. It shows the grain structure of the particles along the dimpled surfaces, and bonding between particles and substrate. Metallurgical bonding is even more evident in FIG. 7.

Figure 7:
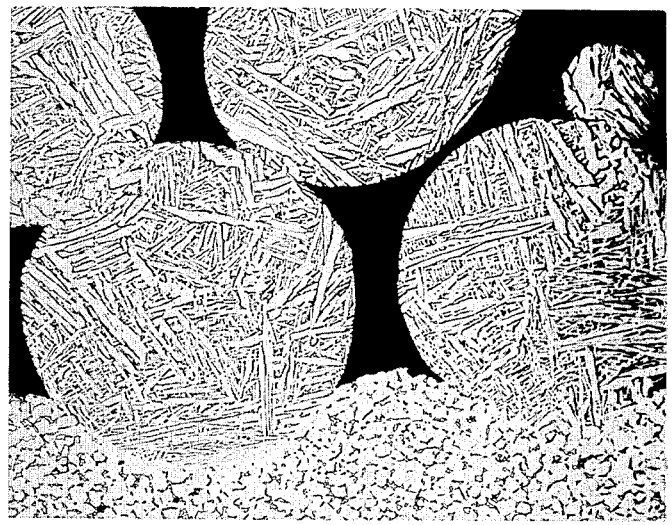
FIG. 7 is a further enlargement (250×) showing bonding at the substrate surface.

While the spheres and substrate shown in FIGS. 4–7 are each the same alloy, FIGS. 6 and 7 illustrate their different granular structures. The substrate remained an alpha worked structure, since bonding of the spheres occurred without raising its temperature above its beta-transus. This is an important aspect of the invention as applied to a prosthesis made from Ti6A14V alloy. It successfully achieves metallurgical bonding of thin coatings without the high temperatures typically required to achieve similar bonding of this alloy by gravity sintering. The process has been shown to successfully substitute mechanical energy in deforming the spheres to replace part of the thermal energy required for metallurgical bonding. This permits coating to be accomplished at reduced temperatures at which the metallurgical properties of the substrate material are not altered.

The coated implant is uniquely recognizable from the enlarged views of the coating material as illustrated in FIGS. 5, 6 and 7. The coating, typically three to six layers thick, includes randomly dispersed discrete metal particles having a substantially uniform size. They are clearly joined to one another and to the substrate by metallurgical bonds. The outermost layer of particles is compressively deformed to present an outer surface of proper dimensions for implant purposes. The particles in the coating are separated by a network of interconnected voids having an average size greater than the average size of the discrete metal particles. The surface areas of the particles which surround the interconnected voids are dimpled.

EXAMPLE 4

FIGS. 11 through 16 illustrate features of a prototype prosthesis 40 and a complementary punch and die set for producing a porous coating about a selected coated region on the prosthesis 40 using the method steps generally described above. FIGS. 17 through 20 are flow diagrams detailing the actual production steps used.

Figure 14:
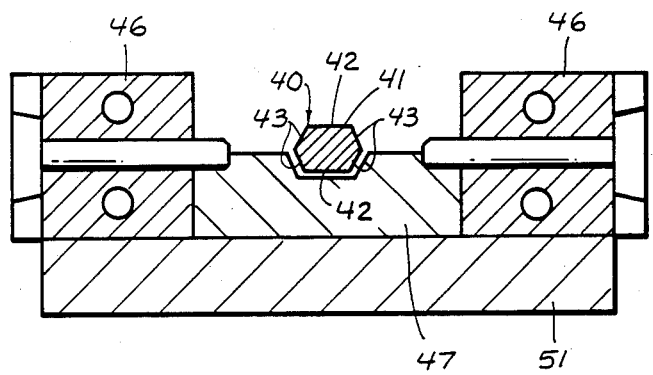
FIG. 14 is a sectional view taken along line 14—14 in FIG. 13.

The punch and die set shown in FIGS. 13 and 14 was designed around the prototype prosthesis 40 shown in FIGS. 11 and 12. The prosthesis design was selected to provide for interface with the tooling, good dimensional control of the coating region, which is shown as recessed shank area 41 in FIG. 11, and ease in manufacturing. The punch and die set shown in FIGS. 13 and 14 also required good dimensional control plus the ability to be assembled and disassembled readily.

The supporting shank of the prosthesis 40 has a six-sided cross-sectional configuration which extends through the recessed shank area 41 that serves as the coated region of the prosthesis. The substrate surfaces to be coated include opposed flats 42 bounded by intersecting angular sides 43. After coating, the flats 42 and angular sides 43 are covered with a porous metallic coating 44 (FIG. 12) presenting outer surfaces that are a continuation of the adjacent solid metal surfaces along the prosthesis 40.

The design of the punch and die set (FIGS. 13 and 14) provided for the prosthesis 40 to be fixed at both ends of the coated region between two split end blocks 45. FIG. 13 shows the punch and die set with the upper end blocks and upper punch removed from the assembly.

Figure 15:
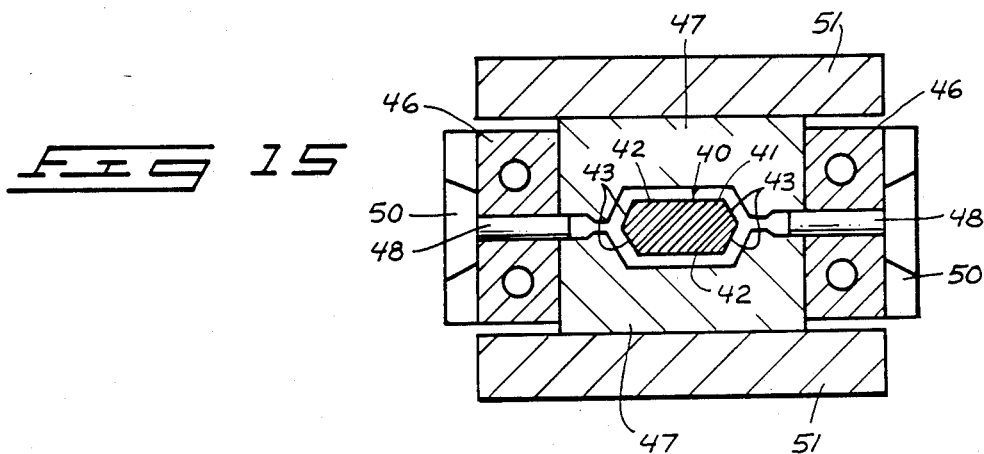
FIG. 15 is a schematic view illustrating initial pressing of the coating materials.
Figure 16:
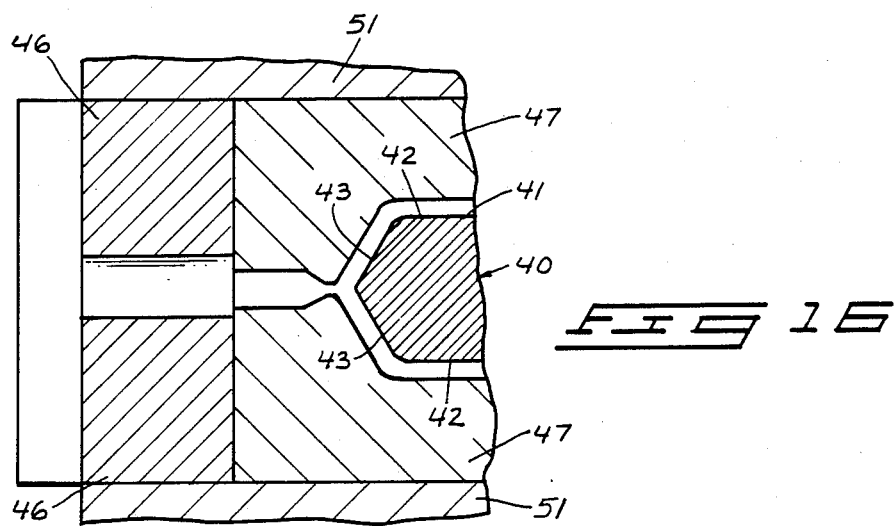
FIG. 16 is an enlarged fragmentary schematic view illustrating final pressing.

The end blocks 45 are bolted to opposed die side walls 46. The inwardly facing surfaces of end blocks 45 and side walls 46 interface with movable jaws or punches 47, which are guided by them for opposed movement toward one another and toward prosthesis 40 for compression purposes. Punch positioner pins 48 protrude inwardly beyond the side walls 46 to limit the inward travel of punches 47 during preforming of the coating on prosthesis 40. This is schematically illustrated in FIG. 15. At this preform position of the punches 47, the outer surfaces of the punches 47 extend slightly beyond the side walls 46, which accommodates subsequent final compression of the coating, as shown in FIG. 16.

Final compressive movement of punches 47 is only possible after removal of the punch positioner pins 48. This can be accomplished by manually pulling pin supports 50 attached to the pins 48. The opposed load support plates 51 can then compress the punches 47 to the fixed stops defined by the outer surfaces of side walls 46 (FIG. 16). This will result in the coating thickness about prosthesis 40 being at the selected nominal thickness about the entire coated region 41 on prosthesis 40. It is to be noted that in the closed position (FIG. 16) a parting gap is provided between punches 47 at each side of the prosthesis 40. This gap should be selected to provide adequate room for a single layer of the microspheres or coating particles to pass through it without being crushed.

FIG. 17 is a flow diagram of the process used in fabricating a porous coating on the hip prosthesis illustrated i FIG. 12. The microspheres are first weighed, blended with binder, and placed on each punch 47 prior to assembly of the punch and die set about the receiving prosthesis 40. The blended mixture can be spread manually by a blade, or can be ejected from a container. The amount of the blended mixture spread over the punch surfaces should be slightly in excess of that required for the coating. The punches 47 are then assembled in the die and pushed together until the fixed loading stops are contacted. After vacuum hot pressing, the coated prosthesis is removed from the tooling and any radiusing or blending of contour along the corners and edges can be accomplished by hand or machine prior to removal of the iron microspheres in acid.

A detailed flow sheet for the preparation of the coating is given in FIG. 18. A very important benefit of using a binder is the fact that the two different types of microspheres can be mixed uniformly and do not separate as they might when dry mixed. A mixture of Klucel type L binder is mixed with alcohol to produce the binder solution. This particular binder was chosen for prototype use because the literature indicates that it would leave the least residual material after hot pressing. The use of alcohol, rather than water, assists in preventing rusting of the iron microspheres in the binder solution.

It was observed in earlier tests that a few of the iron microspheres remained in the coating after final etching of the bonded coating. This occurred because they apparently had an iron oxide coating that prevented the acid solution from dissolving them. To eliminate this problem, the iron microspheres should be initially etched in a solution of one part hydrochloric acid, one part water, and four percent formaldehyde (37% neutralized solution). This will remove the iron oxide coating that might be present on some of the microspheres. It also passivates the iron surface and prevents further oxidation. Immediately after etching, the microspheres are thoroughly rinsed in alcohol.

The two types of microspheres are weighed and blended with a binder solution before being spread onto the surfaces of each punch 47. A controlled quantity of the blended materials should be applied to each punch. The punches are then inserted into the die containing the prosthesis and cold-pressed to a positive stop defined by the interposed pins 48.

FIG. 19 is a detailed flow sheet of the steps involved in densification of the coating materials and substrate bonding. The loaded die is placed in a vacuum hot press, pre-heated, pressed at temperature, cooled and removed from the hot press. As noted above, it is preferable that heating and cooling steps be accomplished without substantial compression loading of the die assembly.

Figure 20:
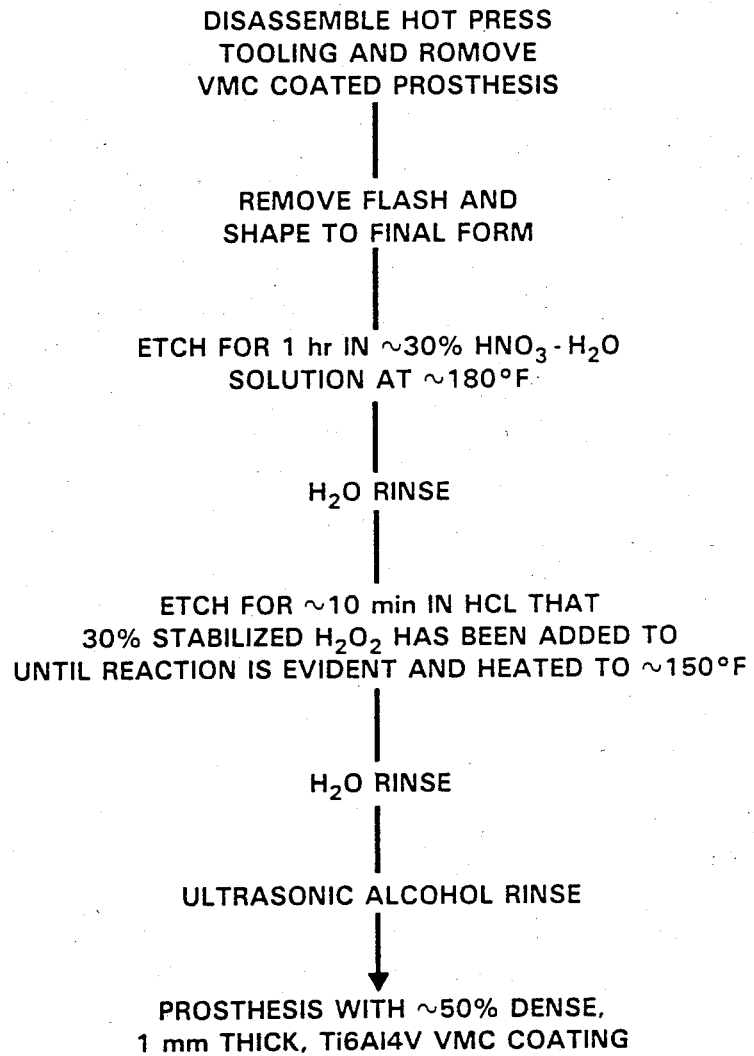

FIG. 20 is a detailed flow sheet for the post-densification processing of the coated prosthesis. It is removed from the tooling, shaped to final form, and etched in two solutions to remove the iron microspheres.

The resulting coating, shown in FIG. 12, will exhibit the metallography illustrated in FIGS. 5 through 7. The bonded coating particles will present indentations remaining where the iron microspheres have been removed by etching. The outer coating surface will include flattened areas that are reproductions of the surfaces at the interior of the respective punches 47. Diffusion bonding occurs between adjacent coating particles and also between the substrate surface of the prosthesis 40 and those particles in contact with it. The substrate is clearly indented by both the coating particles and by the removed iron particles.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A method of producing a porous coating for tissue ingrowth applications on a preselected metallic substrate area of a prosthesis, comprising the following steps:
    covering the metallic substrate area of the prosthesis with a blended mixture of primary particles and secondary particles, said primary particles being metallic and capable of metallurgically bonding to the substrate area, said secondary particles being solid phase and capable of mechanically supporting the primary particles in a matrix;
    raising the temperature of the mixture and metallic substrate area to an elevated temperature at which metallurgical bonding of the primary particles can occur under compression and at which melting of the secondary particles or reactions between the primary and secondary particles does not occur;
    compressing the mixture against the metallic substrate area while at the elevated temperature to metallurgically bond the contacting primary particles and portions of the substrate area as a result of the combination of elevated temperature and compression to which they are subjected; and
    removing the expendable secondary particles to present a homogeneously porous coating on the metallic substrate area in which bonded primary particles are separated from one another by a network of interconnected voids.

2. The method of claim 1, wherein the step of covering the metallic substrate area comprises:
    mixing a preselected proportion of primary and secondary particles with a binder in a homogenously blended mixture; and
    applying the blended mixture of particles and binder onto the metallic substrate area at a dimensional thickness greater than that of the resulting porous coating.

3. The method of claim 2 wherein the step of applying the blended mixture is accomplished by first spreading the mixture over surface areas of punches complementary to the metallic substrate area.

4. The method of claim 1 wherein the step of covering the metallic substrate area comprises:
   mixing a preselected proportion of primary and secondary particles with a binder in a homogenously blended mixture;
   applying the blended mixture of particles and binder onto the metallic substrate area at a dimensional thickness greater than that of the resulting porous coating; and
   curing the binder to secure the blended mixture of primary and secondary particles onto the metallic substrate area.

5. The method of claim 1 wherein the blended mixture of primary and secondary particles is maintained in a homogeneous state by adding to it a liquid binder prior to covering the metallic substrate area of the prosthesis.

6. The method of claim 1 wherein the metallic substrate area of the prosthesis and the primary particles are each composed of Ti6A14V alloy;
   said elevated temperature being below the beta transus temperature for the alloy.

7. A method of producing a porous coating for tissue ingrowth applications on a preselected metallic substrate area of a prosthesis, comprising the following steps:
   positioning the prosthesis within a mold cavity with the metallic substrate area spaced inwardly from the mold cavity surfaces;
   filling the space between the metallic substrate area and mold cavity surfaces with a blended mixture of primary particles and secondary particles, said primary particles being metallic and capable of metallurgically bonding to the substrate area, said secondary particles being solid phase and capable of mechanically supporting the primary particles in a matrix;
   heating the prosthesis and mixture of particles to an elevated temperature at which metallurgical bonding can occur between adjacent primary particles and between the primary particles and the metallic substrate area under compression and at which melting of the secondary particles or reactions between the primary and secondary particles does not occur;
   compressing the mixture of particles against the metallic substrate area while at the elevated temperature to deform the primary particles and the portions of the metallic area engaged thereby and to metallurgically bond the contacting primary particles and portions of the substrate area as a result of the combination of elevated temperature and compression to which they are subjected; and
   subsequently removing the secondary particles from the resulting matrix of bonded primary particles to present a homogenously porous coating on the metallic substrate area in which bonded primary particles are separated from one another by a network of interconnected voids.

8. The method of claim 7 wherein the compressing step reduces the thickness of the coating by 10% to 30%.

9. The method of claim 7 wherein the step of filling the space between the metallic substrate area and mold cavity surfaces is accomplished by directing a dry blend of primary and secondary particles between them.

10. The method of claim 7 wherein the step of filling the space between the metallic substrate area and mold cavity surfaces is accomplished by directing a dry blend of primary and secondary particles between them; and
    bonding the primary particles to one another and to the metallic substrate area by gravity sintering prior to compressing them while at the elevated temperature.

11. The method of claim 7 wherein the step of filling the space between the metallic substrate area and mold cavity surfaces is accomplished by directing a blend of primary and secondary particles between them, plus a liquid binder.

12. The method of claim 7 wherein the step of filling the space between the metallic substrate area and mold cavity surfaces is accomplished by directing a homogeneously blended mixture of a binder and primary and secondary particles between them.

13. The method of claim 7 wherein the step of filling the space between the metallic substrate area and mold cavity surfaces is accomplished by directing a homogeneously blended mixture of a binder and primary secondary particles between them; and
    curing the binder to thereby attach the primary and secondary particles to the metallic substrate area prior to compressing them at the elevated temperature.

14. The method of claim 7 wherein the step of filling the space between the metallic substrate area and mold cavity surfaces is accomplished by spreading a homogeneously blended mixture of a binder and primary and secondary particles over the mold cavity surfaces prior to positioning the prosthesis within the mold cavity formed thereby.

15. A method of producing a porous coating for tissue ingrowth applications on a preselected metallic substrate area of a prosthesis, comprising the following steps:
    positioning the prosthesis within a mold cavity with the preselected substrate area spaced inwardly from the mold cavity surfaces by a distance of approximately 0.5 to 1.5 millimeters while also filling the space between the preselected substrate area and mold cavity surfaces with a blended mixture of primary spherical particles and secondary spherical particles,, said primary particles being metallic and capable of metallurgically bonding to the substrate area, said secondary particles being solid phase and capable of mechanically supporting the primary particles in a matrix; the primary and secondary spherical particles having a narrow range of diameters less than 0.5 millimeters;
    heating the spherical particles within the mold to an elevated temperature at which metallurgical bonding can occur between the individual primary spherical particles under compression and at which melting of the secondary particles or reactions between the primary and secondary particles does not occur;
    compressing the primary and secondary spherical particles against the preselected substrate area of the prosthesis while at the elevated temperature to metallurgically bond the primary particles as a result of a combination of the elevated temperature and compression to which they are subjected; and removing the expendable material from the resulting coating.

16. The method of claim 15 wherein the compressing step produces the desired surface configuration on the coating about the preselected substrate area of the prosthesis.

17. The method of claim 15 further comprising the step of bonding the primary particles to one another and to the metallic substrate area by gravity sintering prior to compressing them while at the elevated temperature.

18. The method of claim 15 further comprising the step of bonding the primary particles to one another and to the metallic substrate area by gravity sintering prior to compressing them while at the elevated temperature; and the compressing step being carried out by hot isostatic pressing or by compression within a multiple-segment die.

19. The method of claim 15 wherein the expendable material is removed by chemical processing steps.

20. The method of claim 15 wherein the metallic substrate area of the prosthesis and the primary particles are each composed of Ti6A14V alloy;

said elevated temperature being below the beta transus temperature for the alloy.

21. A prosthesis for tissue ingrowth applications, comprising:

a structural metallic substrate; and a coating in the form of a matrix presented by randomly dispersed discrete metal particles having a substantially uniform size joined to one another and to the substrate by metallurgical bonds, the particles and substrate being compressibly deformed to present an outer coating surface conforming to the size and configuration of a mold in which they were compressed and of proper dimensions for implant purposes without machining;

the metal particles being separated from one another by a network of interconnected voids having an average size greater than the average size of the discrete metal particles to present a homogeneously porous coating about the substrate.

22. The prosthesis of claim 21 wherein the discrete metal particles are substantially spherical;

both the substrate and particles being composed of a Ti6A14V alloy, the substrate having an alpha phase content.

23. A prosthesis having a porous coating for tissue ingrowth applications on a preselected metallic substrate area, wherein the coating is produced by the following method steps:

covering the metallic substrate area of the prosthesis with a blended mixture of primary particles and secondary particles, said primary particles being metallic and capable of metallurgically bonding to the substrate area, said secondary particles being solid phase and capable of mechanically supporting the primary particles in a matrix;

raising the temperature of the mixture and metallic substrate area to an elevated temperature at which metallurgical bonding of the primary particles can occur under compression and at which melting of the secondary particles or reactions between the primary and secondary particles does not occur;

compressing the mixture against the metallic substrate area while at the elevated temperature to metallurgically bond the contacting primary particles and portions of the substate area as a result of the combination of elevated temperature and compression to which they are subjected; and removing the expendable secondary particles to present a homogenously porous coating on the metallic substrate area in which bonded primary particles are separated from one another by a network of interconnected voids.

24. A prosthesis having a porous coating for tissue ingrowth applications on a preselected metallic substrate area, wherein the coating is produced by the following method steps:

positioning the prosthesis within a mold cavity with the metallic substrate area spaced inwardly from the mold cavity surfaces;

filling the space between the metallic substrate area and mold cavity surfaces with a blended mixture of primary particles and secondary particles, said primary particles being metallic and capable of metallurgically bonding to the substrate area, said secondary particles being solid phase and capable of mechanically supporting the primary particles in a matrix;

heating the prosthesis and mixture of particles to an elevated temperature at which metallurgical bonding can occur between adjacent primary particles and between the primary particles and the metallic substrate area under compression and at which melting of the secondary particles or reactions between the primary and secondary particles does not occur;

compressing the mixture of particles against the metallic substrate area while at the elevated temperature to deform the primary particles and the portions of the metallic area engaged thereby and to metallurgically bond the contacting primary particles and portions of the substrate area as a result of the combination of elevated temperature and compression to which they are subjected; and subsequently removing the secondary particles from the resulting matrix of bonded primary particles to present a homogenously porous coating on the metallic substrate area in which bonded primary particles are separated from one another by a network of interconnected voids.

25. The prosthesis of claim 24 wherein the metallic substrate area of the prosthesis and the primary particles are each composed of Ti6A14V alloy;

said elevated temperature being below the beta transus temperature for the alloy.

* * * * *